United States Patent [19]
Bandman et al.

[11] Patent Number: 6,018,028
[45] Date of Patent: Jan. 25, 2000

[54] HUMAN PROTEASOME SUBUNIT PROTEINS

[75] Inventors: Olga Bandman, Mountain View; Janice Au-Young, Berkeley; Jennifer L. Hillman, San Jose; Surya K. Goli, Sunnyvale, all of Calif.

[73] Assignee: Incyte Pharmaceuticals, Inc., Palo Alto, Calif.

[21] Appl. No.: 09/134,591

[22] Filed: Aug. 13, 1998

Related U.S. Application Data

[62] Division of application No. 08/701,935, Aug. 23, 1996, Pat. No. 5,843,715.

[51] Int. Cl.⁷ .................................................. C07K 14/47
[52] U.S. Cl. ............................................................ 530/350
[58] Field of Search ............................................. 530/350

*Primary Examiner*—Elizabeth Kemmerer
*Assistant Examiner*—David S. Romeo
*Attorney, Agent, or Firm*—Leanne C. Price, Esq.; Incyte Pharmaceuticals, Inc.

[57] ABSTRACT

The present invention provides polynucleotides which identify and encode novel human proteasome subunit proteins. The invention provides for genetically engineered expression vectors and host cells comprising the nucleic acid sequences encoding PSUB. The invention also provides for the use of substantially purified PSUB, antagonists, and in pharmaceutical compositions for the treatment of diseases associated with the expression of PSUB. Additionally, the invention provides for the use of antisense molecules to PSUB in pharmaceutical compositions for treatment of diseases associated with the expression of PSUB. The invention also describes diagnostic assays which utilize diagnostic compositions comprising the polynucleotide, fragments or the complement thereof, which hybridize with the genomic sequence or the transcript of polynucleotides encoding PSUB or anti-PSUB antibodies which specifically bind to PSUB.

2 Claims, 18 Drawing Sheets

```
5' ATG GCG GCT GTG TCG GTG TAT GCT CCA GTT GGA GGC TTC TCT TTT GAT AAC
    M   A   A   V   S   V   Y   A   P   V   G   G   F   S   F   D   N
                    9          18          27          36         45         54

TGC CGC AGG AAT GCC GTC TTG GAA GCC GAT TTT GCA AAG AGG GGA TAC AAG CTT
    C   R   R   N   A   V   L   E   A   D   F   A   K   R   G   Y   K   L
                   63          72          81          90         99        108

CCA AAG GTC CGG AAA ACT GGC ACC ATC GCT GGG GTG GTC TAT AAG GAT GGC
    P   K   V   R   K   T   G   T   I   A   G   V   V   Y   K   D   G
                  117         126         135         144        153        162

ATA GTT CTT GGA GCA GAT ACA CAC TTC ATA TCT CCT AAT ATG GTT GCT GAC AAG
    I   V   L   G   A   D   T   H   F   I   S   P   N   M   V   A   D   K
                  171         180         189         198        207        216

AAC TGT TCA AAA ATA TAT TGT GGT GCT GGG
    N   C   S   K   I   Y   C   G   A   G
                  225         234         243         252        261        270

ACA GCT GCA GAC ACA ATG ACA ACC CAG CTC ATT TCT TCC AAC CTG GAG CTC
    T   A   A   D   T   M   T   T   Q   L   I   S   S   N   L   E   L
                  279         288         297         306        315        324

CAC TCC CTC TCC ACT GGC CGT CTT CCC AGA GTT GTG ACA GCC AAT CGG ATG CTG
    H   S   L   S   T   G   R   L   P   R   V   V   T   A   N   R   M   L
                  333         342         351         360        369        378
```

FIGURE 1A

```
                387         396         405         414         423         432
AAG CAG ATG CTT TTC AGG TAT CAA GGT TAC ATT GGT GCA GCC CTA GTT TTA GGG
 K   Q   M   L   F   R   Y   Q   G   Y   I   G   A   A   L   V   L   G 441         450         459         468         477         486
GGA GTA GAT GTT ACT GGA CCT CAC CTC TAC AGC ATC TAT CCT CAT GGA TCA ACT
 G   V   D   V   T   G   P   H   L   Y   S   I   Y   P   H   G   S   T 495         504         513         522         531         540
GAT AAG TTG CCT TAT GTC ACC ATG GGT TCT GGC TTG GCA GCA ATG GCT GTA
 D   K   L   P   Y   V   T   M   G   S   G   L   A   A   M   A   V 549         558         567         576         585         594
TTT GAA GAT AAG TTT AGG CCA GAC ATG GAG GAG TCC TTG GCA GAA GCC AAG AAT CTG GGT
 F   E   D   K   F   R   P   D   M   E   E   S   L   A   E   A   K   N   L   G 603         612         621         630         639         648
GAG CGA AGC ATC GCA GCT GGC ATC TTC AAC GAC CTG GGC TCC GGA AGC AAC ATT
 E   R   S   I   A   A   G   I   F   N   D   L   G   S   G   S   N   I 657         666         675         684         693         702
GAC CTC TGC GTC ATC AGC AAG AAC AAG CTG GAT TTT CTC CGC TAC ACA GTG
 D   L   C   V   I   S   K   N   K   L   D   F   L   R   Y   P   Y   T   V 711         720         729         738         747         756
CCC AAC AAG GGG ACC AGG CTT KGC CGG TAC AGG TGT GAG AAA GGG ACT WCT
 P   N   K   G   T   R   L   X   R   Y   R   C   E   K   G   T   X
```

FIGURE 1B

```
     765             774             783             792             801             810
GCA GTC CTN ACT GNG AAA TTA CTC CNC TTG NGA TTT NAG GTN CTT GAG NAC AGT
 A   V   L   T   X   K   L   L   X   L   X   F   X   V   L   E   X   S 819             828             837
CAA ACA ATT GGC ANT TCN TGA ATT GGA TTA A 3'
 Q   T   I   G   X   S
```

FIGURE 1C

```
                      9          18          27          36          45          54
5' GGC AGC GCA GGA CAC GGC GCC GAG GGT GGK GCG CGG GCC TAG TGG CGC CGG GAG 63          72          81          90          99         108
   TCG CGG GTG CGC GCG GGC CGT GAG GGC TGT GCG CTT TTG AGA GTC GCG GCG GAA GGA 117         126         135         144         153         162
   GCC CGG CCG CCC GCC GGC ATG AGC TAC GAC CGC GCC ATC ACC GTC TTC TCG
                            M   S   Y   D   R   A   I   T   V   F   S 171         180         189         198         207         216
   CCC GAC GGC CAC CTC TTC CAA GTG GAG TAC GCG CAG GAG GCC GTC AAG AAG GGC
    P   D   G   H   L   F   Q   V   E   Y   A   Q   E   A   V   K   K   G 225         234         243         252         261         270
   TCG ACC GCG GTT GGT GTT CGA GGA AGA GAC ATT GTT CTT GGT GTG GAG AAG
    S   T   A   V   G   V   R   G   R   D   I   V   L   G   V   E   K 279         288         297         306         315         324
   AAG TCA GCC AAA CTG CAG GAT GAA AGA ACA GTG CGG AAG ATC TGT GCT TTG
    K   S   A   K   L   Q   D   E   R   T   V   R   K   I   C   A   L 333         342         351         360         369         378
   GAT GAC AAC GTC TGC ATG GCC TTT GCA GGC TTA ACC GCC GAT GCA AGG ATA GTC
    D   D   N   V   C   M   A   F   A   G   L   T   A   D   A   R   I   V
```

FIGURE 2A

```
ATC AAC AGG GCC CGG GTG GAG TGC CAG AGC CAC CGG ACT GTG GAG GAC CCG
 I   N   R   A   R   V   E   C   Q   S   H   R   L   T   V   E   D   P
387                 396         405         414         423         432

GTC ACT GTG GAG TAC ATC ACC CGC TAC ATC GCC AGT CTG AAG CAG CGT TAT ACG
 V   T   V   E   Y   I   T   R   Y   I   A   S   L   K   Q   R   Y   T
441                 450         459         468         477         486

CAG AGC AAT GGG CGC AGG CCG TTT GGC ATC TCT GCC CTC ATC GTG GGT TTC GAC
 Q   S   N   G   R   R   P   F   G   I   S   A   L   I   V   G   F   D
495                 504         513         522         531         540

TTT GAT GGC ACT CCT AGG CTC TAT CAG ACT GAC CCC TCG GGC ACA TAC CAT GCC
 F   D   G   T   P   R   L   Y   Q   T   D   P   S   G   T   Y   H   A
549                 558         567         576         585         594

TGG AAG GCC AAT GGG ATA GGC CGG AAG GGT GCC TCA GTG CGT GAG TTC CTG GAG
 W   K   A   N   G   I   G   R   K   G   A   S   V   R   E   F   L   E
603                 612         621         630         639         648

AAG AAC TAT ACT GAC GAA GCC ATT GAA ACA GAT CTG ACC ATT AAG CTG GTG
 K   N   Y   T   D   E   A   I   E   T   D   L   T   I   K   L   V
657                 666         675         684         693         702

ATC AAG GCA CTC CTG GAA GTG CAG TCA GGT GGC AAA AAC ATT GAA CTT GCT
 I   K   A   L   L   E   V   Q   S   G   G   K   N   I   E   L   A
711                 720         729         738         747         756
```

FIGURE 2B

```
     765            774            783            792            801            810
GTC ATG AGG CGA GAT CAA TCC CTC AAG ATT TTA AAT CCT GAA GAA ATT GAG AAG
 V   M   R   R   D   Q   S   L   K   I   L   N   P   E   E   I   E   K 819            828            837            846            855            864
TAT GTT GCT GAA ATT GAA AAA GAA AAC GAA GAA AAG AAA CAA AAG
 Y   V   A   E   I   E   K   E   N   E   E   K   K   Q   K 873            882            891            900            909            918
AAA GCA TCA TGA TGA ATA AAA TGT CTT TGC TTG TAA TTT TTA AAT TCA TAT CAA
 K   A   S 927            936            945            954            963            972
TCA TGG ATG AGT CTC GAT GTG TAG GCC TTT CCA TTC CAT TTA TTC ACA CTG AGT 981            990            999
GTC CTA CAA TAA ACT TCC GTA TTT TTA ACC TGT  3'
```

FIGURE 2C

The Electronic Northern for Clone: 620494
and Stringency >= 50

| Library | Lib Description | Abun | Pct Abun |
|---|---|---|---|
| LVENNOT02 | heart, left ventricle, 39 M | 1 | 0.2088 |
| ADRENOT01 | adrenal gland, 10-46 M/F | 2 | 0.2081 |
| FIBRNGT01 | GD23A fibroblasts, radiation 5 min | 1 | 0.1664 |
| PTHYTUM01 | parathyroid tumor, adenoma, M/F, NORM, WM | 4 | 0.1111 |
| PROSTUT03 | prostate tumor, 67 M, match to PROSNOT05 | 3 | 0.1055 |
| THYRNOT01 | thyroid, 64 F | 4 | 0.0911 |
| BRAINOT04 | brain, choroid plexus, hemorrhage, 44 M | 2 | 0.0711 |
| HMC1NOT01 | HMC-1 mast cell line, 52 F | 2 | 0.0666 |
| BSTMNON02 | brain stem, 72 M, NORM | 2 | 0.0637 |
| OVARNOT02 | ovary, 59 F | 2 | 0.0630 |
| COLNNOT13 | colon, ascending, 28 M | 2 | 0.0621 |
| PROSNOT06 | prostate, 57 M, match to PROSTUT04 | 4 | 0.0595 |
| COLNNOT05 | colon, 40 M, match to COLNCRT01 | 2 | 0.0577 |
| HNT2AGT01 | hNT-2 cell line, post-mitotic neurons | 3 | 0.0570 |
| UTRSNOT06 | uterus, myometrium, 50 F | 2 | 0.0565 |
| HNT2RAT01 | hNT-2 cell line, teratocarcinoma, treated RA | 3 | 0.0556 |
| BLADNOT04 | bladder, 28 M | 2 | 0.0555 |
| LUNGNOT04 | lung, 2 M | 3 | 0.0549 |
| BRAINOM03 | brain, 55 M, NORM, WM | 2 | 0.0540 |
| BRAITUT01 | brain tumor, oligoastrocytoma, 50 F | 4 | 0.0537 |
| BLADTUT05 | bladder tumor, 66 M | 2 | 0.0536 |
| KIDNTUT01 | kidney tumor, Wilms, 8m F | 2 | 0.0533 |
| MMLR2DT01 | macrophages (adher PBMNC), M/F, 48-hr MLR | 3 | 0.0531 |

FIGURE 3A

| | | |
|---|---|---|
| BLADNOT05 | bladder, 60 M, match to BLADTUT04 | 2 0.0528 |
| BRSTNOM01 | breast, F, NORM, WM | 2 0.0528 |
| LIVRTUT01 | liver tumor, metastasis, 51 F | 2 0.0518 |
| UCMCL5T01 | mononuclear cells, treated IL-5 | 4 0.0500 |
| MENITUT03 | brain tumor, benign meningioma, 35 F | 2 0.0499 |
| U937NOT01 | U937 monocyte cell line, 37 M | 1 0.0496 |
| BMARNOT03 | bone marrow, 16 M | 2 0.0484 |
| PROSNOT15 | prostate, 66 M, match to PROSTUT10 | 2 0.0483 |
| RATRNOT02 | heart, right atrium, 39 M | 2 0.0472 |
| LVENNOT01 | heart, left ventricle, 51 F | 1 0.0450 |
| LUNGFEM01 | lung, fetal, NORM, WM | 3 0.0444 |
| COLNTUT02 | colon tumor, 75 M, match to COLNNOT01 | 2 0.0440 |
| HUVENOB01 | HUVEC endothelial cell line, control | 1 0.0419 |
| LIVSFEM02 | liver/spleen, fetal M, NORM, WM | 15 0.0399 |
| KERANOT02 | keratinocytes, primary cell line, 30 F | 1 0.0396 |
| UTRSNOT01 | uterus, 59 F | 1 0.0393 |
| STOMTUT01 | stomach tumor, 52 M, match to STOMNOT02 | 1 0.0367 |
| LPARNOT02 | parotid gland, 70 M | 1 0.0324 |
| KIDNNOT05 | kidney, neonatal F | 2 0.0322 |
| FIBRSEM01 | fibroblasts, senescent, NORM, WM | 1 0.0312 |
| PGANNOT03 | paraganglia, 46 M | 1 0.0311 |
| THYRNOT02 | thyroid, hyperthyroidism, 16 F | 1 0.0303 |
| LUNGAST01 | lung, asthma, 17 M | 2 0.0300 |
| COLNNOT16 | colon, 62 M, match to COLNTUT03 | 1 0.0295 |
| PANCTUT02 | pancreatic tumor, carcinoma, 45 F | 1 0.0289 |
| MELANOM01 | melanocytes, M, NORM, WM | 3 0.0288 |
| PANCNOT07 | pancreas, fetal M | 1 0.0287 |
| COLNFET02 | colon, fetal F | 2 0.0286 |

FIGURE 3B

| | | | |
|---|---|---|---|
| PROSNOT11 | prostate, 28 M | 1 | 0.0282 |
| BEPINON01 | bronchial epithelium, primary cell line, 54 M, NORM | 1 | 0.0274 |
| BRAITUT12 | brain tumor, astrocytoma, 40 F, match to BRAINOT14 | 1 | 0.0272 |
| PROSTUT10 | prostate tumor, 66 M, match to PROSNOT15 | 1 | 0.0268 |
| COLNNOT23 | colon, 16 M | 1 | 0.0264 |
| BRAINOT09 | brain, fetal M | 1 | 0.0262 |
| BRAITUT13 | brain tumor, meningioma, 68 M | 1 | 0.0262 |
| LUNGNOT10 | lung, fetal M | 1 | 0.0261 |
| LUNGNOT14 | lung, 47 M | 1 | 0.0259 |
| STOMFET01 | stomach, fetal F | 1 | 0.0255 |
| KERANOT01 | keratinocytes, neonatal M | 1 | 0.0228 |
| TMLR2DT01 | lymphocytes (non-adher PBMNC), M/F, 24-hr MLR | 1 | 0.0211 |
| LUNGNOT03 | lung, 79 M, match to LUNGTUT02 | 1 | 0.0200 |
| THYMNOT02 | thymus, 3 M | 1 | 0.0193 |
| UTRSNOT02 | uterus, 34 F | 1 | 0.0166 |
| PROSTUT04 | prostate tumor, 57 M, match to PROSNOT06 | 1 | 0.0163 |
| PGANNOT01 | paraganglia, 46 M | 1 | 0.0160 |
| NGANNOT01 | ganglioneuroma, 9 M | 1 | 0.0155 |
| BRAITUT03 | brain tumor, astrocytoma, 17 F | 1 | 0.0153 |
| CORPNOT02 | brain, corpus callosum, Alzheimer's, 74 M | 1 | 0.0153 |
| BRSTTUT01 | breast tumor, 55 F, match to BRSTNOT02 | 1 | 0.0151 |
| BRSTNOT03 | breast, 54 F, match to BRSTTUT02 | 1 | 0.0147 |
| LATRTUT02 | heart tumor, myoma, 43 M | 1 | 0.0137 |
| BLADTUT04 | bladder tumor, 60 M, match to BLADNOT05 | 1 | 0.0127 |
| BRAINOM01 | brain, infant F, NORM, WM | 2 | 0.0089 |
| PLACNOM02 | placenta, neonatal F, NORM, WM | 1 | 0.0056 |

Electronic Northern Results returned a total of 77 row(s).

FIGURE 3C

The Electronic Northern for Clone: 669671
and Stringency = 50

| Library | Lib Description | Abun | Pct Abun |
|---|---|---|---|
| PANCDIT03 | pancreas, NIDDM, 57 M | 1 | 0.146 |
| TONGTUT01 | tongue tumor, carcinoma, 36 M | 4 | 0.118 |
| COCHFEM01 | ear, cochlea, fetal, WM | 1 | 0.116 |
| BRSTNOT01 | breast, 56 F | 6 | 0.115 |
| TESTNOT03 | testis, 37 M | 2 | 0.112 |
| TESTNOT04 | testis, 37 M | 1 | 0.107 |
| AMLBNOT01 | AML blast cells, blast crisis, 58 F | 1 | 0.105 |
| CORNNOT01 | corneal fibroblasts, 76 yr old | 1 | 0.100 |
| PANCNOT07 | pancreas, fetal M | 3 | 0.085 |
| PITUNOT01 | pituitary, 16-70 M/F | 2 | 0.085 |
| COLNTUT03 | colon tumor, 62 M, match to COLNNOT16 | 3 | 0.082 |
| BEPINON01 | bronchial epithelium, primary cell line, 54 M, NORM | 3 | 0.082 |
| THP1NOB01 | THP-1 promonocyte cell line, control | 2 | 0.066 |
| STOMNOT01 | stomach, 55 M | 2 | 0.060 |
| COLNNOT16 | colon, 62 M, match to COLNTUT03 | 2 | 0.059 |
| SYNORAT05 | synovium, knee, rheumatoid, 62 F | 2 | 0.057 |
| BMARNOT02 | bone marrow, 16-70 M/F | 2 | 0.054 |
| EOSIHET02 | eosinophils, hypereosinophilia, 48 M | 5 | 0.052 |
| KIDNNOT02 | kidney, 64 F | 1 | 0.048 |
| FIBRNOT01 | WI38 lung fibroblast cell line, fetal F | 1 | 0.047 |
| TMLR3DT01 | lymphocytes (non-adher PBMNC), M, 96-hr MLR | 2 | 0.046 |

FIGURE 4A

| | | |
|---|---|---|
| BRSTNOT03 | breast, 54 F, match to BRSTTUT02 | 3 | 0.044 |
| BMARNOR02 | bone marrow, 16-70 M/F, RP | 1 | 0.043 |
| THYRNOT03 | thyroid tumor, adenoma, 28 F | 3 | 0.041 |
| MYOMNOT01 | uterus, myometrium, 43 F | 1 | 0.041 |
| MUSCNOT02 | muscle, psoas, 12 M | 1 | 0.038 |
| TLYMNOR01 | lymphocytes (non-adher PBMNC), 24 M, RP | 1 | 0.037 |
| HUVESTB01 | HUVEC endothelial cell line, shear stress | 1 | 0.036 |
| SPLNFET01 | spleen, fetal | 1 | 0.035 |
| PROSNOT01 | prostate, 78 M | 1 | 0.035 |
| PROSNOT07 | prostate, 69 M, match to PROSTUT05 | 1 | 0.035 |
| LVENNOT03 | heart, left ventricle, 31 M | 1 | 0.034 |
| HMC1NOT01 | HMC-1 mast cell line, 52 F | 1 | 0.033 |
| BRSTNOT04 | breast, 62 F | 1 | 0.032 |
| PGANNOT03 | paraganglia, 46 M | 1 | 0.031 |
| BRSTNOT05 | breast, 58 F, match to BRSTTUT03 | 2 | 0.031 |
| COLNNOT13 | colon, ascending, 28 M | 1 | 0.031 |
| BRAITUT03 | brain tumor, astrocytoma, 17 F | 2 | 0.031 |
| THYRNOT02 | thyroid, hyperthyroidism, 16 F | 1 | 0.030 |
| LUNGFET03 | lung, fetal F | 2 | 0.027 |
| LUNGNOM01 | lung, 72 M, WM | 1 | 0.027 |
| LUNGNOT10 | lung, fetal M | 1 | 0.026 |
| MPHGNOT03 | macrophages (adher PBMNC), M/F | 2 | 0.026 |
| LIVRNOM01 | liver, 49 M, WM | 1 | 0.025 |
| COLNTUT02 | colon tumor, 75 M, match to COLNNOT01 | 1 | 0.022 |
| PANCNOT01 | pancreas, 29 M | 1 | 0.021 |
| CRBLNOT01 | brain, cerebellum, 69 M | 1 | 0.019 |
| CERVNOT01 | cervix, 35 F | 1 | 0.019 |
| HNT2AGT01 | hNT-2 cell line, post-mitotic neurons | 1 | 0.019 |

FIGURE 4B

| | | |
|---|---|---|
| BRAINOT03 | brain, 26 M | 1 | 0.018 |
| LUNGNOT04 | lung, 2 M | 1 | 0.018 |
| MMLR2DT01 | macrophages (adher PBMNC), M/F, 48-hr MLR | 1 | 0.018 |
| SYNORAT04 | synovium, wrist, rheumatoid, 62 F | 1 | 0.017 |
| SYNORAT03 | synovium, wrist, rheumatoid, 56 F | 1 | 0.017 |
| UTRSNOT02 | uterus, 34 F | 1 | 0.017 |
| KIDNNOT05 | kidney, neonatal F | 1 | 0.016 |
| BRSTTUT01 | breast tumor, 55 F, match to BRSTNOT02 | 1 | 0.015 |
| LUNGAST01 | lung, asthma, 17 M | 1 | 0.015 |
| BRSTTUT03 | breast tumor, 58 F, match to BRSTNOT05 | 1 | 0.015 |
| BRAITUT08 | brain tumor, astrocytoma , 47 M | 1 | 0.015 |

The Northern Link Info returned a total of 60 results.

FIGURE 4C

```
  1  M A A V S V Y A P P V G G F S F D N C R R N A V L E A D F A K R G Y K L P K V R   SEQ ID NO-1
  1  M L K P A L - - E P R G G F S F E N C Q R N A S L E R V L P - - G L K V P H A R   SEQ ID NO-5

41  K T G T T I A G V V Y K D G I V L G A D T R A T E G M V V A D K N C S K I H F I   SEQ ID NO-1
 37  K T G T T I A G L V F Q D G V I L G A D T R A T N D S V V A D K S C E K I H F I   SEQ ID NO-5

81  S P N I Y C C G A G T A A D T D M T T Q L I S S N L E L H S L S T G R L P R V V   SEQ ID NO-1
 77  A P K I Y C C G A G V A A D A E M T T R M V A S K M E L H A L S T G R E P R V A   SEQ ID NO-5

121  T A N R M L K Q M L F R Y Q G Y I G A A L V L G G V D V T G P H L Y S I Y P H G   SEQ ID NO-1
117  T V T R I L R Q T L F R Y Q G H V G A S L I V G G V D L T G P Q L Y G V H P H G   SEQ ID NO-5

161  S T D K L P Y V T M G S G S L A A M A V F E D K F R P D M E E E A K N L G E R     SEQ ID NO-1
157  S Y S R L P F T A L G S G Q D A A L A V L E D R F Q P N M T L E A A Q G L L V E   SEQ ID NO-5

201  S I A A G I F N D L G S G S N I D L C V I S K N K L D F L R P Y T V P N K K G T   SEQ ID NO-1
197  A V T A G I L G D L G S G G N V D A C V I T K T G A K L L R T L S S P T E P V K   SEQ ID NO-5

241  R L X R Y R C E K G T X A V L T X K L L X L X F X V L E X S - Q T I G X S         SEQ ID NO-1
237  R S G R Y H F V P G T T A V L T Q T V K P L T L E L V E E T V Q A M E V E         SEQ ID NO-5
```

FIGURE 5

```
  1 M S Y D R A I T V F S P D G H L F Q V E Y A Q E A V K K G S T A V G V R G R D I    SEQ ID NO-3
  1 M S Y D R A I T V F S P D G H L F Q V E Y A Q E A V K K G S T A V G V R G R D I    SEQ ID NO-6

41 V V L G V E K K S V A K L Q D E R T V R K I C A L D D N V C M A F A - - - - -      SEQ ID NO-3
 41 V V L G V E K K S V A K L Q D E R T V R K I C A L D D N V C M A F A V V A S V S    SEQ ID NO-6

75 G L T A D A R I V I N R A R V E C Q S H R L T V E D P V T V E Y I T R Y I A S L    SEQ ID NO-3
 81 G L T A D A R I V I N R A R V E C Q S H R L T V G D P V T V E Y I T R Y I A S L    SEQ ID NO-6

115 K Q R Y T Q S N G R R P F G I S A L I V G F D F D G T P R L Y Q T D P S G T Y H    SEQ ID NO-3
121 K Q R Y T Q S N G R R P F G I S A L I V G F D F D G T P R L Y Q T D P S G T Y H    SEQ ID NO-6

155 A W K A N A I G R G A K S V R E F L E K N Y T D E A I E T D D L T I K L V I K A    SEQ ID NO-3
161 A W K A N A I G R G A K S V R E F L E K N Y T D D A I E T D D L T I K L V I K A    SEQ ID NO-6

195 L L E V V Q S G G K N I E L A V M R R D Q S L K I L N P E E I E K Y V A E I E K    SEQ ID NO-3
201 L L E V V Q S G G K N I E L A V M R R D Q P L K I L S P E E I E K Y V A E I E K    SEQ ID NO-6

235 E K E E N E K K Q K K A S                                                          SEQ ID NO-3
241 E K E E N E K K K Q K K A S                                                        SEQ ID NO-6
```

FIGURE 6

HUMAN PROTEASOME SUBUNIT PROTEINS

This application is a divisional application of U.S. application Ser. No. 08/701,935, filed Aug. 23, 1996, U.S. Pat. No. 5,843,715.

FIELD OF THE INVENTION

The present invention relates to nucleic acid and amino acid sequences of novel human proteasome subunit proteins and to the use of these sequences in the diagnosis, study, prevention and treatment of disease.

BACKGROUND OF THE INVENTION

Proteasomes are large ring- or cylinder-shaped multicomponent complexes common to all eukaryotic cells (Tanaka et al (1995) New Biol 4: 173–187). They have at least three distinct endopeptidase activities which include hydrolysis of peptide bonds on the carboxyl side of hydrophobic, basic, and acidic amino acid residues (Rivett A J (1993) Biochem J 291: 1–10). Proteasomes, through their protein degradation activity, have been implicated in several important cell functions, including DNA repair, cell cycle progression, signal transduction, transcription, and antigen presentation (Finley D et al (1991) Annu Rev Cell Biol 7: 25–69).

Proteasome subunits are encoded by a family of homologous genes. The 20S proteasome consists of a family of 14 different subunits that are classified into 7 different but homologous α-type or B-type subunits (Yang Y et al (1995) J Biol Chem 270: 27687–27694). Changes in the composition of the 20S proteasome are correlated with changes in substrate specificity. Three B-type subunits, LMP2, LMP7, and MECL-1 are upregulated by interferon gamma, and replace their constitutive counterparts, delta and MB-1, in the complex (Larsen F et al (1993) Hum Mol Genet 2: 1589–1595); Martinez CK et al (1991) Nature 353: 664–667; Akiyama K et al (1994) Science 265: 1231–1234). It has been suggested that incorporation of these subunits into the proteasome may generate so called "immunoproteasomes" that could represent a proteasomal subpopulation capable of more efficiently processing protein antigens into the short peptides that are transferred to the class I major histocompatibility complex (MHC) for presentation on the cell surface to cytotoxic lymphocytes (Tanaka K (1994) J Leuk Biol 56: 571–575). An example of the α-type subfamily of proteasome subunits, RC6-I, cloned from rat cells by Ni R et al (1995, Biochim Biophys Acta 1264: 45–52), is expressed in all the rat tissues examined, yet may also contribute to the diversity of proteasome functions.

Proteasomes and Disease

A decrease in muscle mass, known as muscle wasting or cachexia, has been shown to be associated with the proteasome-dependent proteolytic system. Rats bearing the Yoshida AH-130 ascites hepatoma for 7 days showed a significant decrease in muscle mass in relation to non-tumor bearing controls (Llovera M et al (1995) Int J Cancer 61: 138–141). The muscle wasting was found to be associated with an increased proteolytic rate related to the proteasome-dependent proteolytic system. Muscle wasting is common among human cancer patients. In addition to cancer, proteasome-dependent muscle wasting is also influenced by nutritional manipulation (such as fasting and dietary protein deficiency), muscle activity and disuse, AIDS, and the pathological conditions, sepsis, trauma; and acidosis (Attaix D et al (1994) Reprod Nutr Dev 34: 583–597).

The presence of proteasome-dependent proteolysis has been detected in patients affected by neurodegenerative diseases such as Alzheimer's disease. Whereas the intracellular amyloid beta-protein precursor (APP) did not show appreciable proteasome-mediated degradation, three extracellular APP forms were degraded by this proteolytic pathway, suggesting a potential regulatory role for the proteasome-mediated system in the in vivo APP metabolic pathway (Gregori L et al (1994) Biochem Biophys Res Commun 203: 1731–1738). Paired helical filaments (PHF) are fibrillar structures that accumulate in degenerating neurons in the brains of Alzheimer's disease patients. One component of PHF, the PHF-smear, consists of the tau protein fragment tagged for proteasomal degradation (Morishima M et al (1994) Dementia 5: 282–288).

Evidence from experiments on mouse and rabbit reticulocytes indicate that proteasome degradation is a key rate-limiting step in antigen presentation (Grant EP et al (1995) J Immunol 155: 3750–3758). The rates of degradation of beta-galactosidase constructs correlated with the rates of class I antigen presentation in vivo. This shows that proteasome degradation pathway may have a critical role in generating MHC class I-presented peptides.

Depletion of specific cellular proteins may have many medical and agricultural benefits. Redirecting the proteasome-dependent proteolytic pathway may facilitate specific protein removal. Thus, it may be possible to design proteasome subunits capable of directing the selective removal of many intracellular proteins, such as those implicated in the pathogenesis of Alzheimer's disease. The selective modulation of proteasome activity may allow successful management of the diseases associated with protein degradation, such as muscle wasting syndrome, and diseases in which undesired proteins may be targeted for degradation, such as viral infections and cancer. A newly discovered proteasome subunit may have novel specificity and could thus target a unique set of proteins for degradation.

More than a million Americans suffer from dementia, a permanent and often progressive decline in intellectual function that substantially interferes with a person's social and economic activity. Alzheimer's disease is a major cause of dementia and its prevalence is growing. Currently, there are no known treatments that stop or reverse the relentless progression in the impairment of mental abilities of patients afflicted with Alzheimer's disease. Similarly, there are no known treatments that fully reverse muscle wasting, a disorder common among a growing number of AIDS patients. New proteasome subunit proteins could satisfy a need in the art by providing new means of diagnosing and treating Alzheimer's disease and muscle wasting syndrome.

SUMMARY OF THE INVENTION

The present invention discloses two novel human proteasome subunit proteins (hereinafter referred to individually as PSUBA and PSUBB, and collectively as PSUB), characterized as having homology to human putative proteasome subunit MECL-1 (GI 406227) and rat proteasome subunit RC6-I (GI 1089797), respectively. Accordingly, the invention features two substantially purified proteasome subunit proteins, having the amino acid sequence shown in SEQ ID NO:1 and SEQ ID NO:3, and having characteristics of proteasome subunit proteins.

One aspect of the invention features isolated and substantially purified polynucleotides which encode PSUB. In a particular aspect, the polynucleotide is the nucleotide sequence of SEQ ID NO:2 or SEQ ID NO:4. In addition, the invention features polynucleotide sequences that hybridize under stringent conditions to SEQ ID NO:2 or SEQ ID NO:4.

The invention further relates to nucleic acid sequences encoding PSUB, oligonucleotides, peptide nucleic acids (PNA), fragments, portions or antisense molecules thereof, and expression vectors and host cells comprising polynucleotides which encode PSUB. The present invention also relates to antibodies which bind specifically to PSUB, pharmaceutical compositions comprising substantially purified PSUB, fragments thereof, or antagonists of PSUB, in conjunction with a suitable pharmaceutical carrier, and methods for producing PSUB, fragments thereof, or antagonists of PSUB.

BRIEF DESCRIPTION OF THE FIGURES

FIGS. 1A–1C show the amino acid sequence (SEQ ID NO:1) and nucleic acid sequence (SEQ ID NO:2) of the novel proteasome subunit protein, PSUBA. The alignment was produced using MacDNAsis software (Hitachi Software Engineering Co Ltd, San Bruno, Calif.).

FIGS. 2A–2C show the amino acid sequence (SEQ ID NO:3) and nucleic acid sequence (SEQ ID NO:4) of the novel proteasome subunit protein, PSUBB (MacDNAsis software, Hitachi Software Engineering Co Ltd).

FIGS. 3A and 3B show the northern analysis for the consensus sequence (SEQ ID NO:2). The northern analysis was produced electronically using LIFESEQ™ database (Incyte Pharmaceuticals, Palo Alto Calif.).

FIGS. 4A and 4B show the northern analysis for the consensus sequence (SEQ ID NO:4) (LIFESEQ™ database, Incyte Pharmaceuticals, Palo Alto Calif.).

FIG. 5 shows the amino acid sequence alignments between PSUBA (SEQ ID NO:1) and MECL-1 (GI 307307; SEQ ID NO:5), produced using the multisequence alignment program of DNAStar software (DNAStar Inc, Madison Wis.).

FIG. 6 shows the amino acid sequence alignments between PSUBB (SEQ ID NO:3) and RC6-1 (GI 1089797; SEQ ID NO:6), produced using the multisequence alignment program of DNAStar software (DNAStar Inc, Madison Wis.).

DETAILED DESCRIPTION OF THE INVENTION

Definitions

Figure 7:
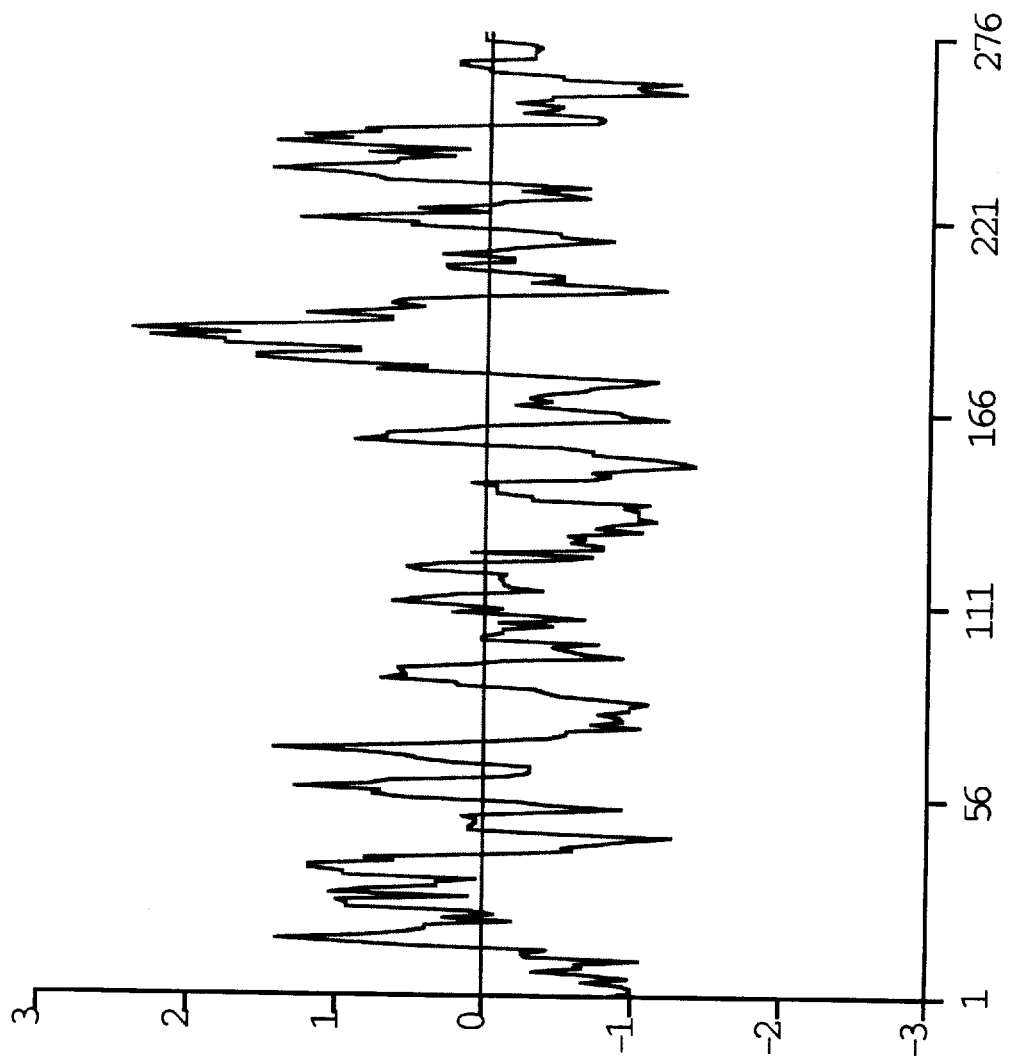
FIG. 7 shows the hydrophobicity plot (generated using MacDNAsis software) for PSUBA, SEQ ID NO:1; the X axis reflects amino acid position, and the negative Y axis, hydrophobicity (FIGS. 7, 8, 9, and 10).

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

As used herein, PSUB refers to the amino acid sequences of substantially purified PSUB obtained from any species, particularly mammalian, including bovine, ovine, porcine, murine, equine, and preferably human, from any source whether natural, synthetic, semi-synthetic or recombinant.

A "variant" of PSUB is defined as an amino acid sequence that is altered by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

A "deletion" is defined as a change in either amino acid or nucleotide sequence in which one or more amino acid or nucleotide residues, respectively, are absent.

An "insertion" or "addition" is that change in an amino acid or nucleotide sequence which has resulted in the addition of one or more amino acid or nucleotide residues, respectively, as compared to the naturally occurring PSUB.

A "substitution" results from the replacement of one or more amino acids or nucleotides by different amino acids or nucleotides, respectively.

The term "biologically active" refers to a PSUB having structural, regulatory or biochemical functions of a naturally occurring PSUB. Likewise, "immunologically active" defines the capability of the natural, recombinant or synthetic PSUB, or any oligopeptide thereof, to induce a specific immune response in appropriate animals or cells and to bind with specific antibodies.

The term "derivative" as used herein refers to the chemical modification of a nucleic acid encoding PSUB or the encoded PSUB. Illustrative of such modifications would be replacement of hydrogen by an alkyl, acyl, or amino group. A nucleic acid derivative would encode a polypeptide which retains essential biological characteristics of natural PSUB.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm–5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnoloav*, Stockton Press, New York N.Y.). Amplification as carried out in the polymerase chain reaction technologies is described in Dieffenbach C W and G S Dveksler (1995, *PCR Primer, a Laboratory Manual*, Cold Spring Harbor Press, Plainview N.Y.).

Preferred Embodiments

The present invention relates to novel PSUB and to the use of the nucleic acid and amino acid sequences in the study, diagnosis, prevention and treatment of disease.

cDNAs encoding a portion of PSUB were found in cDNA libraries derived from a variety of tissues, including many types of tumors (FIGS. 3A, 3B, 4A, and 4B).

The present invention also encompasses PSUB variants. A preferred PSUB variant is one having at least 80% amino acid sequence similarity to the PSUB amino acid sequence (SEQ ID NO:1), a more preferred PSUB variant is one having at least 90% amino acid sequence similarity to SEQ ID NO:1 and a most preferred PSUB variant is one having at least 95% amino acid sequence similarity to SEQ ID NO:1.

Nucleic acids encoding the human PSUB of the present invention were first identified in cDNA, Incyte Clones 35602 (HUV-EC-C cell cDNA library, HUVENOB01) and 214332 (stomach tissue cDNA library, STOMNOT01), through a computer-generated search for amino acid sequence alignments. A consensus sequence, SEQ ID NO:2, was derived from the following overlapping and/or extended nucleic acid sequences: Incyte Clones 35602 (from cDNA library HUVENOB01); 1001145 (BRSTNOT03); 002693 (HMC1NOT01); 435430 (THYRNOT01); 809510 (LUNGNOT04); 790231 (PROSTUT03); 534318 (LVENNOT02); 099788 (ADRENOT01); 922230 (RATRNOT02); 1259332 (MENITUT03); 790470 (PROSTUT03); 731831 (LUNGNOT03); 1229447 (BRAITUT01); 588885 (UTRSNOT01); 485734 (HNT2RAT01); 620494 (PGANNOT01); 003179 (HMC1NOT01); 792354 (PROSTUT03); 434884 (THYRNOT01); 1257755 (MENITUT03); 523118 (MMLR2DT01); 1371151 (BSTMNON02); 101394 (ADRENOT01); 1216113 (BRSTTUT01); 309168 (TMLR2DT01); 344845 (THYMNOT02); 486678 (HNT2RAT01); 487162 (HNT2AGT01 489670 (HNT2AGT01); 545440 (OVARNOT02); 749432 (BRAITUT01); 825674 (PROSNOT06); 880174 (THYRNOT02). A consensus sequence, SEQ ID NO:4, was derived from the following overlapping and extended nucleic acid sequences: Incyte Clones 214332 (from cDNA library STOMNOT01), 134368 (BMARNOT02); 170669 (BMARNOR02); 264486 (HNT2AGT01); 334102 (EOSIHET02); 681529 (UTRSNOT02); 413676 (BRSTNOT01); 409107 (EOSIHET02); 781117 (MYOMNOT01); 027278 (SPLNFET01); 405286 TMLR3DT01); 031804 (THP1NOB01); 277313 (TESTNOT03); 002781 (HMC1NOT01); 982837 (TONGTUT01); 220319 (STOMNOT01); 198239 (KIDNNOT02); 274887 (PANCDIT03); 411982 (BRSTNOT01); 987519 (LVENNOT03); 413768 (BRSTNOT01); 1215821 (BRSTTUT01); 070405 (HUVESTB01); 897511 (BRSTNOT05); 321105 (EOSIHET02); 767218 (LUNGNOT04); 916549 (BRSTNOT04); 637485 (BRSTNOT03); 1263395 (SYNORAT05); 032700 (THP1NOB01); 142336 (TLYMNOR01); 441677 (MPHGNOT03); 223253 (PANCNOT01); 301433 (TESTNOT04); 410683 (BRSTNOT01); 870638 (LUNGAST01); 984344 (TONGTUT01); 512962 (MPHGNOT03); 860534 (BRAITUT03); 669671 (CRBLNOT01); 095972 (PITUNOT01); 053900 (FIBRNOT01); 094463 (PITUNOT01); 104949 (BMARNOT02); 110405 (AMLBNOT01); 1232644 (LUNGFET03); 1265525 (SYNORAT05); 1281361 (COLNNOT16); 1281769 (COLNNOT16); 276060 (TESTNOT03); 320892 (EOSIHET02); 321162 (EOSIHET02); 402393 (TMLR3DT01); 416831 (BRSTNOT01); 419977 (BRSTNOT01); 479576 (MMLR2DT01); 616847 (COLNTUT02); 631833 (KIDNNOT05); 639689 (BRSTNOT03); 640624 (BRSTNOT03); 704379 (SYNORAT04); 837963 (PROSNOT07); 866442 (BRAITUT03); 881873 (THYRNOT02); 899222 (BRSTTUT03); 932060 (CERVNOT01); 981763 (TONGTUT01). The nucleic acid sequence of SEQ ID NO:2 encodes the PSUBA amino acid sequence, SEQ ID NO:1. The nucleic acid sequence of SEQ ID NO:4 encodes the PSUBB amino acid sequence; SEQ ID NO:3.

Figure 8:
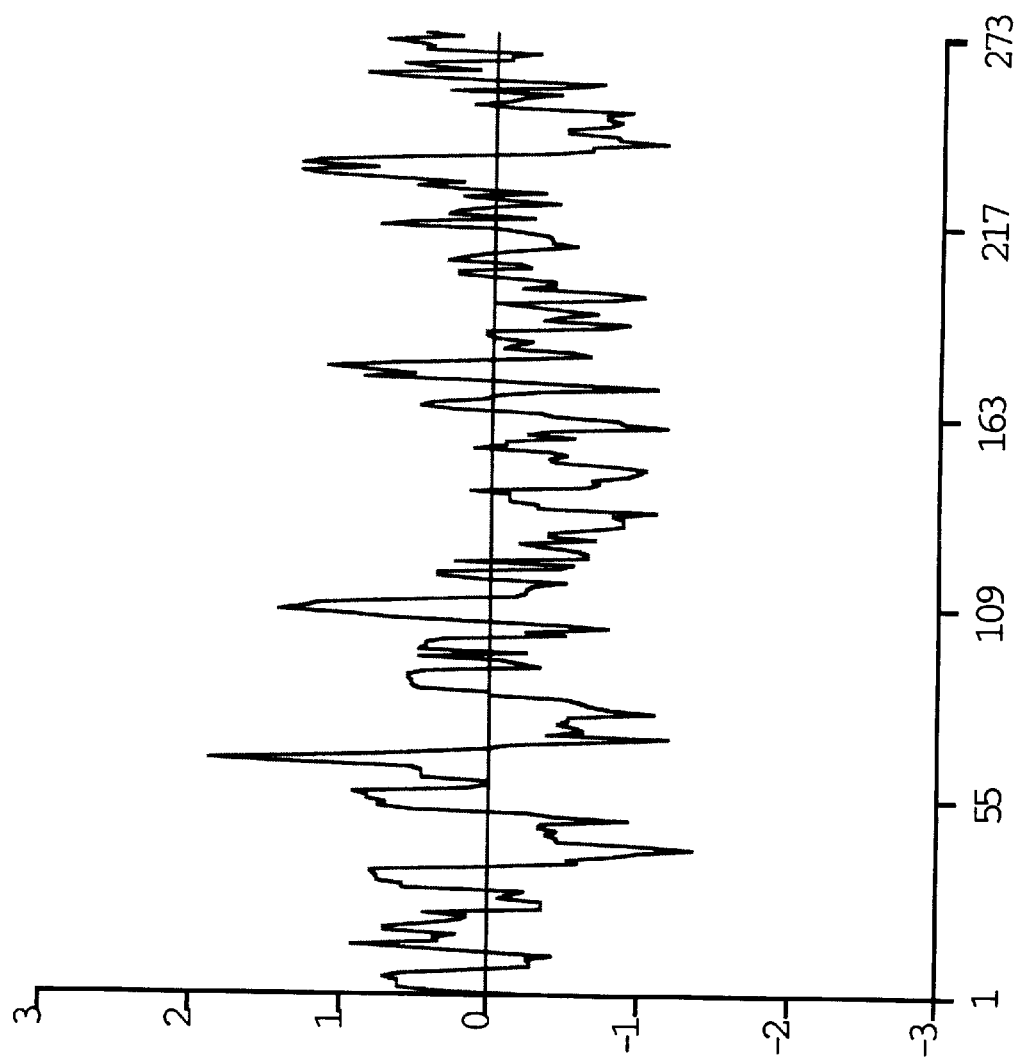
FIG. 8 shows the hydrophobicity plot for MECL-1, SEQ ID NO:5.
Figure 9:
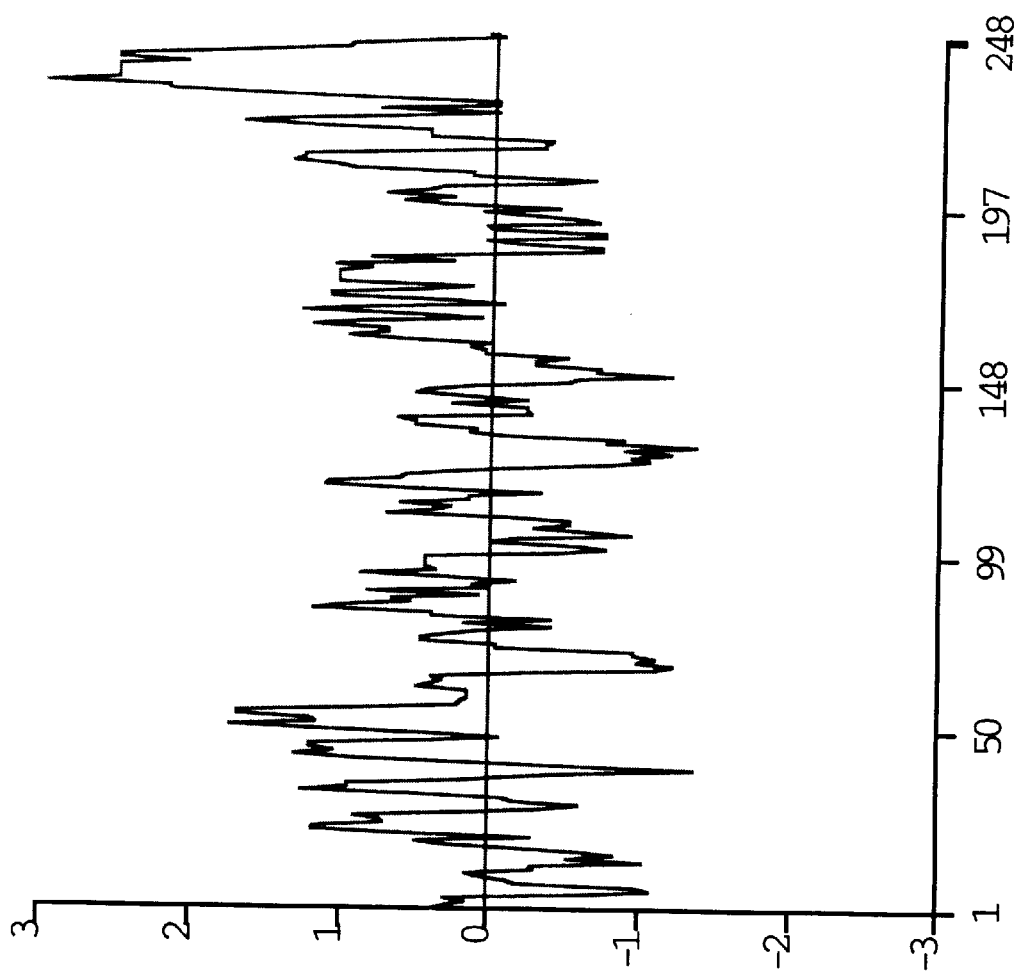
FIG. 9 shows the hydrophobicity plot for PSUBB, SEQ ID NO:3.
Figure 10:
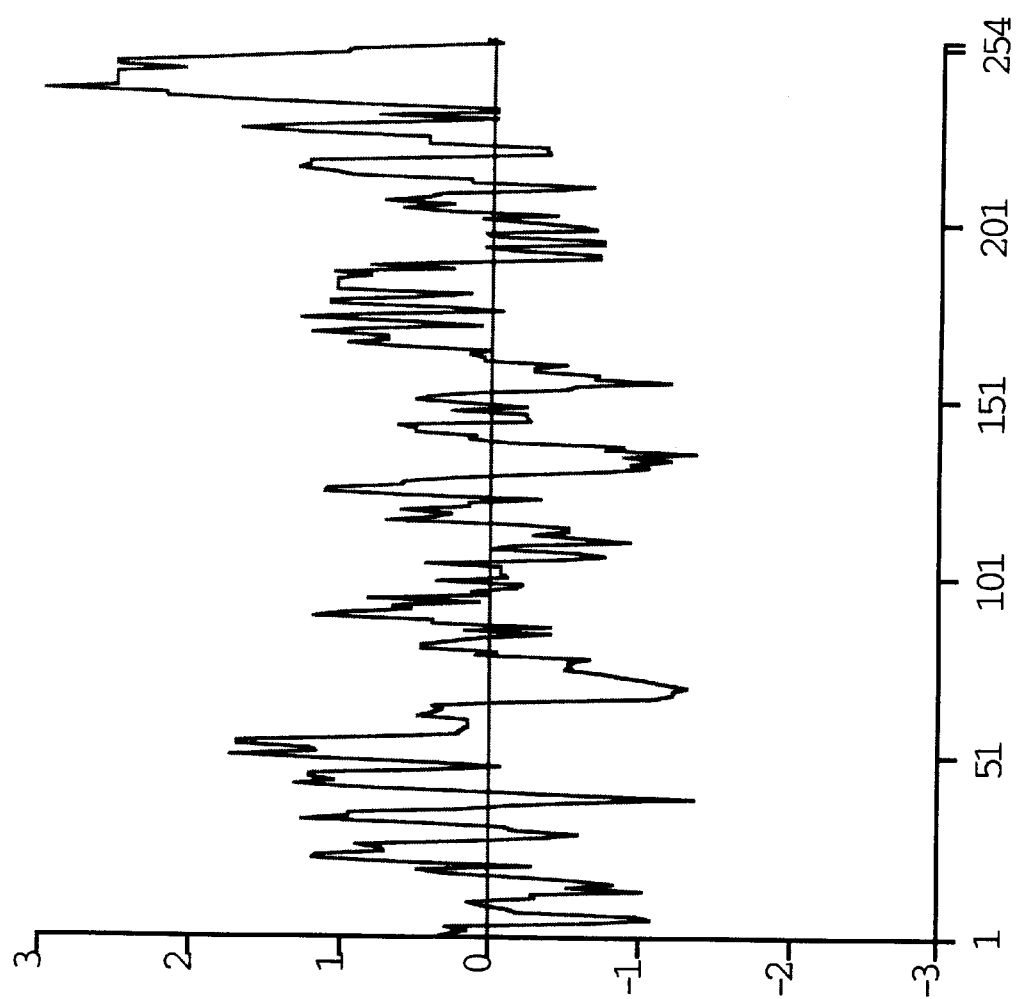
FIG. 10 shows the hydrophobicity plot for RC6-I, SEQ ID NO:6.

The present invention is based, in part, on the chemical and structural homology between PSUBA and the B-type proteasome subunit MECL-1 (GI 406227; Larsen et al, supra); FIG. 5) and between PSUBB and the α-type proteasome subunit RC6-I (GI 1089797; Ni et al 1995, supra; FIG. 6). PSUBA and MECL-1 share 53% identity, whereas PSUBB and RC6-I share 96% identity. As illustrated by FIGS. 7–10, PSUBA and MECL-1, and PSUBB and RC6-I have similar hydrophobicity plots suggesting similar structure. The novel PSUBA is 276 amino acids long and has one potential N glycosylation site. The novel PSUBB is 248 amino acids long and has one potential N glycosylation site.

The PSUB Coding Sequences

The nucleic acid and deduced amino acid sequences of PSUB are shown in FIGS. 1A, 1B, 2A, and 2B. In accordance with the invention, any nucleic acid sequence which encodes the amino acid sequence of PSUB can be used to generate recombinant molecules which express PSUB. In a specific embodiment described herein, a nucleotide sequence encoding a portion of PSUBA was first isolated as Incyte Clones 35602 from a HUV-EC-C cell line cDNA library (HUVENOB01). In another specific embodiment described herein, a nucleotide sequence encoding a portion of PSUBB was first isolated as Incyte Clones 214332 from a stomach tissue cDNA library (STOMNOT01).

It will be appreciated by those skilled in the art that as a result of the degeneracy of the genetic code, a multitude of PSUB-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence of naturally occurring PSUB, and all such variations are to be considered as being specifically disclosed.

Although nucleotide sequences which encode PSUB and its variants are preferably capable of hybridizing to the nucleotide sequence of the naturally occurring PSUB under appropriately selected conditions of stringency, it may be advantageous to produce nucleotide sequences encoding PSUB or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding PSUB and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a PSUB and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding PSUB or any portion thereof.

Also included within the scope of the present invention are polynucleotide sequences that are capable of hybridizing to the nucleotide sequences of FIGS. 1A, 1B, 2A, and 2B under various conditions of stringency. Hybridization conditions are based on the melting temperature (Tm) of the nucleic acid binding complex or probe, as taught in Berger and Kimmel (1987, *Guide to Molecular Clonina Techniaues, Methods in Enzymology*, Vol 152, Academic Press, San Diego Calif.) incorporated herein by reference, and confer may be used at a defined stringency.

Altered nucleic acid sequences encoding PSUB which may be used in accordance with the invention include deletions, insertions or substitutions of different nucleotides resulting in a polynucleotide that encodes the same or a functionally equivalent PSUB. The protein may also show deletions, insertions or substitutions of amino acid residues which produce a silent change and result in a functionally equivalent PSUB. Deliberate amino acid substitutions may be made on the basis of similarity in polarity, charge, solubility, hydrophobicity, hydrophilicity, and/or the amphipathic nature of the residues as long as the biological activity of PSUB is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of PSUB. As used herein, an "allele" or "allelic sequence" is an alternative form of PSUB. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENSE (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding PSUB may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker J D et al (1991; Nucleic Acids Res 19:3055–60). Additionally, one can use, PCR, nested primers and PromoterFinder libraries to walk in genomic DNA (PROMOTERFINDER Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and Sequence NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez M C et al (1993) Anal Chem 65:2851–2858).

Expression of the Nucleotide Sequence

In accordance with the present invention, polynucleotide sequences which encode PSUB, fragments of the polypeptide, fusion proteins or functional equivalents thereof may be used in recombinant DNA molecules that direct the expression of PSUB in appropriate host cells. Due to the inherent degeneracy of the genetic code, other DNA sequences which encode substantially the same or a functionally equivalent amino acid sequence, may be used to clone and express PSUB. As will be understood by those of skill in the art, it may be advantageous to produce PSUB-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of PSUB expression or to produce recombinant RNA transcripts having desirable properties, such as a longer half-life, than transcripts produced from naturally occurring sequence.

The nucleotide sequences of the present invention can be engineered in order to alter a PSUB coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant polynucleotide encoding PSUB may be ligated to a heterologous sequence to encode a fusion protein. For example, for screening of peptide libraries for inhibitors of PSUB activity, it may be useful to encode a chimeric PSUB protein that is recognized by a commercially available antibody. A fusion protein may also be engineered to contain a cleavage site located between a PSUB sequence and the heterologous protein sequence, so that the PSUB may be cleaved and purified away from the heterologous moiety.

In an alternate embodiment of the invention, the coding sequence of PSUB may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a PSUB amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially by preparative high performance liquid chromatography (eg, Creighton (1983) *Proteins, Structures and Molecular Principles*, W H Freeman and Co, New York N.Y.). The composition of the synthetic peptides may be confirmed by amino acid analysis or sequencing (eg, the Edman degradation procedure; Creighton, supra). Additionally the amino acid sequence of PSUB, or any part thereof, may be altered during direct synthesis and/or combined using chemical methods with sequences from other proteins, or any part thereof, to produce a variant polypeptide.

Expression Systems

In order to express a biologically active PSUB, the nucleotide sequence encoding PSUB or its functional equivalent, is inserted into an appropriate expression vector, ie, a vector which contains the necessary elements for the transcription and translation of the inserted coding sequence.

Methods which are well known to those skilled in the art can be used to construct expression vectors containing a PSUB coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York N.Y.

A variety of expression vector/host systems may be utilized to contain and express a PSUB coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of PSUB, vectors based on SV40 or EBV may be used with an appropriate selectable marker.

In bacterial systems, a number of expression vectors may be selected depending upon the use intended for PSUB. For example, when large quantities of PSUB are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the PSUB coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding PSUB may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi R M (1991) Results Probl Cell Differ 17:85–105) may be used. These constructs can be introduced into plant cells by direct DNA transformation or pathogen-mediated transfection. For reviews of such techniques, see Hobbs S or Murry L E in McGraw Hill *Yearbook of Science and Technoloay* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express PSUB is an insect system. In one such system, *Autoarapha californica* nuclear polyhedrosis virus (AcNPV) is used as a vector to express foreign genes in *Spodoptera frugiperda* cells or in Trichoplusia larvae. The PSUB coding sequence may be cloned into a nonessential region of the virus, such as the polyhedrin gene, and placed under control of the polyhedrin promoter. Successful insertion of PSUB will render the polyhedrin gene inactive and produce recombinant virus lacking coat protein. The recombinant viruses are then used to infect *S. fruaiperda* cells or Trichoplusia larvae in which PSUB is expressed (Smith et al (1983) J Virol 46:584; Engelhard E K et al (1994) Proc Nat Acad Sci 91:3224–7).

In mammalian host cells, a number of viral-based expression systems may be utilized. In cases where an adenovirus is used as an expression vector, a PSUB coding sequence may be ligated into an adenovirus transcription/translation complex consisting of the late promoter and tripartite leader sequence. Insertion in a nonessential E1 or E3 region of the viral genome will result in a viable virus capable of expressing PSUB in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a PSUB sequence. These signals include the ATG initiation codon and adjacent sequences. In cases where PSUB, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express PSUB may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman S C and R C Mulligan (1988) Proc Natl Acad Sci 85:8047–51). Recently, the use of visible markers has gained popularity with such markers as anthocyanins, βglucuronidase and its substrate, GUS, and luciferase and its substrate, luciferin, being widely used not only to identify transformants, but also to quantify the amount of transient or stable protein expression attributable to a specific vector system (Rhodes Calif. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the PSUB is inserted within a marker gene sequence, recombinant cells containing PSUB can be identified by the absence of marker gene function. Alternatively, a marker gene can be placed in tandem with a PSUB sequence under the control of a single promoter. Expression of the marker gene in response to induction or selection usually indicates expression of the tandem PSUB as well.

Alternatively, host cells which contain the coding sequence for PSUB and express PSUB may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding PSUB can be detected by DNA-DNA or DNA-RNA hybridization or amplification using probes, portions or fragments of polynucleotides encoding PSUB. Nucleic acid amplification based assays involve the use of oligonucleotides or oligomers based on the PSUB-encoding sequence to detect transformants containing DNA or RNA encoding PSUB. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of PSUB, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PSUB is preferred, but a competitive binding assay may be employed. These and other assays are described, among other places, in Hampton R et al (1990, *Serological Methods, a Laboratory Manual*, APS Press, St Paul Minn.) and Maddox D E et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to polynucleotides encoding PSUB include oligolabeling, nick translation, end-labeling or PCR amplification using a labeled nucleotide. Alternatively, the PSUB sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of PSUB

Host cells transformed with a nucleotide sequence encoding PSUB may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides encoding PSUB can be designed with signal sequences which direct secretion of PSUB through a prokaryotic or eukaryotic cell membrane. Other recombinant constructions may join PSUB to nucleotide sequence encoding a polypeptide domain which will facilitate purification of soluble proteins (Kroll D J et al (1993) DNA Cell Biol 12:441–53; cf discussion of vectors infra containing fusion proteins).

PSUB may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and PSUB is useful to facilitate purification. One such expression vector provides for expression of a fusion protein compromising a PSUB and contains nucleic acid encoding 6 histidine residues followed by thioredoxin and an enterokinase cleavage site. The histidine residues facilitate purification on IMIAC (immobilized metal ion affinity chromotography as described in Porath et al (1992) Protein Expression and Purification 3: 263–281) while the enterokinase cleavage site provides a means for purifying PSUB from the fusion protein.

In addition to recombinant production, fragments of PSUB may be produced by direct peptide synthesis using solid-phase techniques (cf Stewart et al (1969) *Solid-Phase Peptide Synthesis*, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of PSUB may be chemically synthesized separately and combined using chemical methods to produce the full length molecule.

Uses of PSUB

The rationale for use of the nucleotide and polypeptide sequences disclosed herein is based in part on the chemical and structural homology between the novel PSUBA protein disclosed herein and the human proteasome subunit MECL-1 (GI 406227; Larsen et al, supra) and between PSUBB and the rat proteasome subunit RC6-I (GI 1089797; Ni et al, supra).

Accordingly, PSUB or a PSUB derivative may be used to redirect a cell protein degradation apparatus to selectively remove specific proteins, such as those implicated in the pathogenesis of Alzheimer's disease. In conditions where PSUB protein activity is not desirable, cells could be transfected with antisense sequences to PSUB-encoding polynucleotides or provided with antagonists to PSUB. Thus, PSUB antagonists or antisense molecules may be used to reduce harmful protein degradation in such conditions as muscle wasting syndrome.

PSUB Antibodies

PSUB-specific antibodies are useful for the diagnosis of conditions and diseases associated with expression of PSUB. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

PSUB for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of PSUB amino acids may be fused with those of another protein such as keyhole limpet hemocyanin and antibody produced against the chimeric molecule. Procedures well known in the art can be used for the production of antibodies to PSUB.

For the production of antibodies, various hosts including goats, rabbits, rats, mice, etc may be immunized by injection with PSUB or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium paryum* are potentially useful human adjuvants.

Monoclonal antibodies to PSUB may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce PSUB-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PSUB may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse W D et al (1989) Science 256:1275–1281).

A variety of protocols for competitive binding or immunoradiometric assays using either polyclonal or monoclonal antibodies with established specificities are well known in the art. Such immunoassays typically involve the formation of complexes between PSUB and its specific antibody and the measurement of complex formation. A two-site, monoclonal-based immunoassay utilizing monoclonal antibodies reactive to two noninterfering epitopes on a specific PSUB protein is preferred, but a competitive binding assay may also be employed. These assays are described in Maddox D E et al (1983, J Exp Med 158:1211).

Diagnostic Assays Using PSUB Specific Antibodies

Particular PSUB antibodies are useful for the diagnosis of conditions or diseases characterized by expression of PSUB or in assays to monitor patients being treated with PSUB, agonists or inhibitors. Diagnostic assays for PSUB include methods utilizing the antibody and a label to detect PSUB in human body fluids or extracts of cells or tissues. The polypeptides and go antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring PSUB, using either polyclopal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on PSUB is preferred, but a competitive binding assay may be employed. These assays are described, among other places, in Maddox, D E et al (1983, J Exp Med 158:1211).

In order to provide a basis for diagnosis, normal or standard values for PSUB expression must be established. This is accomplished by combining body fluids or cell extracts taken from normal subjects, either animal or human, with antibody to PSUB under conditions suitable for complex formation which are well known in the art. The amount of standard complex formation may be quantified by comparing various artificial membranes containing known quantities of PSUB with both control and disease samples from biopsied tissues. Then, standard values obtained from normal samples may be compared with values obtained from samples from subjects potentially affected by disease. Deviation between standard and subject values establishes the presence of disease state.

Drug Screening

PSUB, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between PSUB and the agent being tested, may be measured.

Another technique for drug screening which may be used provides for high throughput screening of compounds having suitable binding affinity to the PSUB is described in detail in "Determination of Amino Acid Sequence Antigenicity" by Geysen H N, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of PSUB and washed. Bound PSUB is then detected by methods well known in the art. Purified PSUB can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding PSUB specifically compete with a test compound for binding PSUB. In this manner, the antibodies can be used to detect the presence of any peptide which shares one or more antigenic determinants with PSUB.

Uses of the Polynucleotide Encoding PSUB

A polynucleotide encoding PSUB, or any part thereof, may be used for diagnostic and/or therapeutic purposes. For diagnostic purposes, polynucleotides encoding PSUB of this invention may be used to detect and quantitate gene expression in biopsied tissues in which expression of PSUB may be implicated. The diagnostic assay is useful to distinguish between absence, presence, and excess expression of PSUB and to monitor regulation of PSUB levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding PSUB or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring sequences encoding PSUB, alleles or related sequences.

Probes may also be used for the detection of related sequences and should preferably contain at least 50% of the nucleotides from any of these PSUB encoding sequences. The hybridization probes of the subject invention may be derived from the nucleotide sequence of SEQ ID NO:2 or from genomic sequence including promoter, enhancer elements and introns of the naturally occurring PSUB. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs encoding PSUB include the cloning of nucleic acid sequences encoding PSUB or PSUB derivatives into vectors for the production of mRNA probes. Such vectors are known in the art and are commercially available and may be used to synthesize RNA probes La vitro by means of the addition of the appropriate RNA polymerase as T7 or SP6 RNA polymerase and the appropriate radioactively labeled nucleotides.

Polynucleotide sequences encoding PSUB may be used for the diagnosis of conditions or diseases with which the expression of PSUB is associated. For example, polynucleotide sequences encoding PSUB may be used in hybridization or PCR assays of fluids or tissues from biopsies to detect PSUB expression. The form of such qualitative or quantitative methods may include Southern or northern analysis, dot blot or other membrane-based technologies; PCR technologies; dip stick, pIN, chip and ELISA technologies. All of these techniques are well known in the art and are the basis of many commercially available diagnostic kits.

The nucleotide sequences encoding PSUB disclosed herein provide the basis for assays that detect activation or induction associated with Alzheimer's disease and muscle wasting syndrome. The nucleotide sequence encoding PSUB may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding PSUB in the sample indicates the presence of the associated disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for PSUB expression must be established. This is accomplished by combining body fluids or cell extracts taken from normal subjects, either animal or human, with PSUB, or a portion thereof, under conditions suitable for hybridization or amplification. Standard hybridization may be quantified by comparing the values obtained for normal subjects with a dilution series of PSUB run in the same experiment where a known amount of a substantially purified PSUB is used. Standard values obtained from normal samples may be compared with values obtained from samples from patients afflicted with PSUB-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR, as described in U.S. Pat. Nos. 4,683,195 and 4,965,188, provides additional uses for oligonucleotides based upon the PSUB sequence. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. For example, the presence of a relatively high amount of PSUB in extracts of biopsied tissues may indicate the onset of Alzheimer's disease or muscle wasting syndrome. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to genes encoding proteasome subunit proteins and its expression profile, polynucleotide sequences encoding PSUB disclosed herein may be useful in the treatment of conditions such as Alzheimer's disease or muscle wasting syndrome.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense polynucleotides of the gene encoding PSUB. See, for example, the techniques described in Sambrook et al (supra) and Ausubel et al (supra).

The polynucleotides comprising full length cDNA sequence and/or its regulatory elements enable researchers to use sequences encoding PSUB as an investigative tool in sense (Youssoufian H and H F Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding PSUB can be turned off by transfecting a cell or tissue with expression vectors which express high levels of a desired PSUB-encoding fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of gene encoding PSUB, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee J E et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of sequences encoding PSUB.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding PSUB. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for PSUB disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for PSUB can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price C M (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: a Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding PSUB on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example a sequence tagged site based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of PSUB, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful dosee and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

It is contemplated, for example, that PSUB or a PSUB derivative can be delivered in a suitable formulation to block the progression of Alzheimer's disease or muscle wasting syndrome. Similarly, administration of PSUB antagonists may also inhibit the activity or shorten the lifespan of this protein.

The examples below are provided to illustrate the subject invention and are not included for the purpose of limiting the invention.

EXAMPLES

I Construction of cDNA Libraries

HUV-EC-C

The HUVEC cell line is a normal, homogeneous, well characterized early passage endothelial cell culture from human umbilical vein (Cell Systems Corporation, 12815 NE 124th St., Kirkland, Wash. 98034). The cDNA library was custom constructed by Stratagene (11099 M. Torrey Pines Rd., La Jolla, Calif. 92037). Synthesis of cDNA was primed with either oligo dT or random hexamers. Synthetic adaptor oligonucleotides were ligated onto cDNA ends enabling its insertion into UNIZIP vector system (Stratagene), allowing high efficiency unidirectional (sense orientation) lambda library construction and the convenience of a plasmid system with blue/white color selection to detect clones with cDNA insertions.

The cDNA library can by screened with either DNA probes or antibody probes and the pBluescript phagemid (Stratagene) can be rapidly excised in vivo. The phagemid allows the use of a plasmid system for easy insert characterization, sequencing, site-directed mutagenesis, the creation of unidirectional deletions and expression of fusion polypeptides. The custom-constructed library phage particles were infected into *E. coli* host strain XL1-Blue (Stratagene), which has a high transformation efficiency, increasing the probability of obtaining rare, under-represented clones in the cDNA library. Alternative unidirectional vectors include but are not limited to pcDNAI (Invitrogen) and pSHlox-1 (Novagen).

Stomach

The normal stomach used to generate this library was obtained from the Keystone Skin Bank, International Institute for the Advancement of Medicine (Exton, Pa.). Five grams of normal stomach tissue from a 47 year old male was flash frozen, ground in a mortar and pestle, and lysed immediately in buffer containing guanidinium isothiocyanate. Lysis was followed by several phenol chloroform extractions and ethanol precipitation. Poly A+ RNA was isolated using biotinylated oligo d(T) primer and streptavidin coupled to a paramagnetic particle (Promega Corp, Madison Wis.) and sent to Stratagene (11011 North Torrey Pines Road, La Jolla, Calif. 92037). Stratagene prepared the cDNA library using oligo d(T) priming. Synthetic adapter oligonucleotides were ligated onto the cDNA molecules enabling them to be inserted into the UN-ZAP vector system (Stratagene). This allowed high efficiency unidirectional (sense orientation) lambda library construction and the convenience of a plasmid system with blue/white color selection to detect clones with cDNA insertions. The quality of the cDNA library was screened using DNA probes, and then, the pBluescript phagemid (Stratagene) was excised. This phagemid allows the use of a plasmid system for easy insert characterization, sequencing, site-directed mutagenesis, the creation of unidirectional deletions and expression of fusion polypeptides. Subsequently, the custom constructed library phage particles were infected into *E. coli* host strain XL1-Blue (Stratagene). The high transformation efficiency of this bacterial strain increases the probability that the cDNA library will contain rare, under-represented clones. Alternative unidirectional vectors might include, but are not limited to, pcDNAI (Invitrogen) and pSHlox-1 (Novagen).

II Isolation of cDNA Clones

HUV-EC-C

The phagemid forms of individual cDNA clones were obtained by the in vivo excision process, in which the host bacterial strain was coinfected with both the lambda library phage and an f1 helper phage. Polypeptides or enzymes derived from both the library-containing phage and the helper phage nicked the lambda DNA, initiated new DNA synthesis from defined sequences on the lambda DNA and created a smaller, single stranded circular phagemid DNA molecule that included all DNA sequences of the pBluescript plasmid and the cDNA insert. The phagemid carries the gene for B-lactamase, the newly transformed bacteria were selected on medium containing ampicillin.

Phagemid DNA was purified using the MAGIC MINI-PREPS™ DNA Purification System (Promega catalogue #A7100. Promega Corp., 2800 Woods Hollow Rd., Madison, Wis. 53711). This small-scale process provides a simple and reliable method for lysing the bacterial cells and rapidly isolating purified phagemid DNA using a proprietary DNA-binding resin. The DNA was eluted from the purification resin already prepared for DNA sequencing and other analytical manipulations.

Phagemid DNA was also purified using the QIAWELL-8 Plasmid Purification System from QIAGEN, QIAWELL PLUS and QIAWELL ULTRA DNA Purification System (QIAGEN Inc., 9259 Eton Ave., Chatsworth, Calif. 91311). This product line provides a convenient, rapid and reliable high-throughput method for lysing the bacterial cells and isolating highly purified phagemid DNA using QIAGEN anion-exchange resin particles with EMPOREE™ membrane technology from 3M in a multiwell format. The DNA was eluted from the purification resin and prepared for DNA sequencing and other analytical manipulations.

Stomach

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the pBluescript phagemid and the cDNA insert. The phagemid DNA was released from the cells and purified, and used to reinfect fresh host cells (SOLR, Stratagene) where double-stranded phagemid DNA was produced. Because the phagemid carries the gene for b-lactamase, the newly transformed bacteria were selected on medium containing ampicillin. Phagemid DNA was also purified using the QIAWELL-8 Plasmid Purification System from the QIAGEN DNA Purification System (QIAGEN Inc, Chatsworth, Calif.). This product provides a convenient, rapid and reliable high-throughput method for lysing the bacterial cells and isolating highly purified phagemid DNA using QIAGEN anion-exchange resin particles with EMPORE™ membrane technology from 3M in a multiwell format. The DNA was eluted from the purification resin and prepared for DNA sequencing and other analytical manipulations. An alternate method of purifying phagemid has recently become available. It utilizes the Miniprep Kit (Catalog No. 77468, available from Advanced Genetic Technologies Corp., 19212 Orbit Drive, Gaithersburg, Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 1 of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences-containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J Mol Evol 36:290–300; Altschul, S F et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul S F 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of PSUB-Encoding Polynucleotides to Full Length or to Recover Regulatory Elements Full length PSUB-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known PSUB-encoding sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer—primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIA QUICK (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E coli* cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N H). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The PSUB-encoding sequence, or any part thereof, is used to inhibit in vivo or in vitro expression of naturally occurring PSUB. Although use of antisense oligonucleotides, comprising about 20 base-pairs, is specifically described, essentially the same procedure is used with larger cDNA fragments. An oligonucleotide based on the coding sequences of PSUB, as shown in FIGS. 1A, 1B, 2A, and 2B is used to inhibit expression of naturally occurring PSUB. The complementary oligonucleotide is designed from the most unique 5' sequence as shown in FIGS. 1A, 1B, 2A, and 2B and used either to inhibit transcription by preventing promoter binding to the upstream nontranslated sequence or translation of an PSUB-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, 2A, and 2B.

VIII Expression of PSUB

Expression of the PSUB is accomplished by subcloning the cDNAs into appropriate vectors and transfecting the vectors into host cells. In this case, the cloning vector, psport, previously used for the generation of the cDNA library is used to express PSUB in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length PSUB-encoding sequence. The signal sequence directs the secretion of PSUB into the bacterial growth media which can be used directly in the following assay for activity.

IX PSUB Activity

PSUB incorporation into proteasome complexes can be measured by a method described by Yang et al (1995, supra). HtTA cells are transfected with either a PSUB expressing construct or with a negative control. After [$^{35}$S] methionine metabolic labeling, the cells are lysed and proteins are immunoprecipitated with either anti-PSUB antibodies or anti-proteasome antiserum. Gel electrophoresis then reveals the incorporation of PSUB into proteasome complexes.

X Production of PSUB Specific Antibodies

PSUB substantially purified using PAGE electrophoresis (Sambrook, supra) is used to immunize rabbits and to produce antibodies using standard protocols. The amino acid sequence translated from PSUB is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 7 and 9) is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring PSUB Using Specific Antibodies

Naturally occurring or recombinant PSUB is substantially purified by immunoaffinity chromatography using antibodies specific for PSUB. An immunoaffinity column is constructed by covalently coupling PSUB antibody to an activated chromatographic resin such as CnBr-activated Sepharose (Pharmacia Biotech). After the coupling, the resin is blocked and washed according to the manufacturer's instructions.

Media containing PSUB is passed over the immunoaffinity column, and the column is washed under conditions that allow the preferential absorbance of PSUB (eg, high ionic strength buffers in the presence of detergent). The column is eluted under conditions that disrupt antibody/PSUB binding (eg, a buffer of pH 2–3 or a high concentration of a chaotrope such as urea or thiocyanate ion), and PSUB is collected.

XII Identification of Molecules Which Interact with PSUB

PSUB, or biologically active fragments thereof, are labelled with $^{125}$I Bolton-Hunter reagent (Bolton, A E and Hunter, W M (1973) Biochem J 133: 529). Candidate molecules previously arrayed in the wells of a 96 well plate are incubated with the labelled PSUB, washed and any wells with labelled PSUB complex are assayed. Data obtained using different concentrations of PSUB are used to calculate values for the number, affinity, and association of PSUB with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polypeptide comprising the amino acid sequence of SEQ ID NO:1.

2. A composition comprising a substantially purified polypeptide, wherein said polypeptide comprises the amino acid sequence of SEQ ID NO:1, and a suitable carrier.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 276 amino acids
       (B) TYPE: amino acid
       (C) STRANDEDNESS: single
       (D) TOPOLOGY: linear (ii) MOLECULE TYPE: peptide (vii) IMMEDIATE SOURCE:
       (A) LIBRARY:
       (B) CLONE: Consensus (xi) SEQUENCE DESCRIPTION: SEQ ID NO:1:

```
Met Ala Ala Val Ser Val Tyr Ala Pro Pro Val Gly Gly Phe Ser Phe
 1               5                  10                  15

Asp Asn Cys Arg Arg Asn Ala Val Leu Glu Ala Asp Phe Ala Lys Arg
            20                  25                  30

Gly Tyr Lys Leu Pro Lys Val Arg Lys Thr Gly Thr Thr Ile Ala Gly
        35                  40                  45

Val Val Tyr Lys Asp Gly Ile Val Leu Gly Ala Asp Thr Arg Ala Thr
    50                  55                  60

Glu Gly Met Val Val Ala Asp Lys Asn Cys Ser Lys Ile His Phe Ile
65                  70                  75                  80

Ser Pro Asn Ile Tyr Cys Cys Gly Ala Gly Thr Ala Ala Asp Thr Asp
                85                  90                  95

Met Thr Thr Gln Leu Ile Ser Ser Asn Leu Glu Leu His Ser Leu Ser
            100                 105                 110

Thr Gly Arg Leu Pro Arg Val Val Thr Ala Asn Arg Met Leu Lys Gln
        115                 120                 125

Met Leu Phe Arg Tyr Gln Gly Tyr Ile Gly Ala Ala Leu Val Leu Gly
    130                 135                 140

Gly Val Asp Val Thr Gly Pro His Leu Tyr Ser Ile Tyr Pro His Gly
145                 150                 155                 160

Ser Thr Asp Lys Leu Pro Tyr Val Thr Met Gly Ser Gly Ser Leu Ala
                165                 170                 175

Ala Met Ala Val Phe Glu Asp Lys Phe Arg Pro Asp Met Glu Glu Glu
            180                 185                 190

Glu Ala Lys Asn Leu Gly Glu Arg Ser Ile Ala Ala Gly Ile Phe Asn
        195                 200                 205

Asp Leu Gly Ser Gly Ser Asn Ile Asp Leu Cys Val Ile Ser Lys Asn
    210                 215                 220

Lys Leu Asp Phe Leu Arg Pro Tyr Thr Val Pro Asn Lys Lys Gly Thr
225                 230                 235                 240

Arg Leu Xaa Arg Tyr Arg Cys Glu Lys Gly Thr Xaa Ala Val Leu Thr
                245                 250                 255

Xaa Lys Leu Leu Xaa Leu Xaa Phe Xaa Val Leu Glu Xaa Ser Gln Thr
            260                 265                 270

Ile Gly Xaa Ser
        275
```

(2) INFORMATION FOR SEQ ID NO:2:

```
      (i) SEQUENCE CHARACTERISTICS:
          (A) LENGTH: 842 base pairs
          (B) TYPE: nucleic acid
          (C) STRANDEDNESS: single
          (D) TOPOLOGY: linear (ii) MOLECULE TYPE: cDNA (vii) IMMEDIATE SOURCE:
          (A) LIBRARY:
          (B) CLONE: Consensus (xi) SEQUENCE DESCRIPTION: SEQ ID NO:2:

GATGGCGGCT GTGTCGGTGT ATGCTCCACC AGTTGGAGGC TTCTCTTTTG ATAACTGCCG       60

CAGGAATGCC GTCTTGGAAG CCGATTTTGC AAAGAGGGGA TACAAGCTTC CAAAGGTCCG      120

GAAAACTGGC ACGACCATCG CTGGGGTGGT CTATAAGGAT GGCATAGTTC TTGGAGCAGA      180

TACAAGAGCA ACTGAAGGGA TGGTTGTTGC TGACAAGAAC TGTTCAAAAA TACACTTCAT      240

ATCTCCTAAT ATTTATTGTT GTGGTGCTGG ACAGCTGCA GACACAGACA TGACAACCCA       300

GCTCATTTCT TCCAACCTGG AGCTCCACTC CCTCTCCACT GGCCGTCTTC CCAGAGTTGT      360

GACAGCCAAT CGGATGCTGA AGCAGATGCT TTTCAGGTAT CAAGGTTACA TTGGTGCAGC      420

CCTAGTTTTA GGGGAGTAG ATGTTACTGG ACCTCACCTC TACAGCATCT ATCCTCATGG       480

ATCAACTGAT AAGTTGCCTT ATGTCACCAT GGGTTCTGGC TCCTTGGCAG CAATGGCTGT      540

ATTTGAAGAT AAGTTTAGGC CAGACATGGA GGAGGAGGAA GCCAAGAATC TGGGTGAGCG      600

AAGCATCGCA GCTGGCATCT TCAACGACCT GGGCTCCGGA AGCAACATTG ACCTCTGCGT      660

CATCAGCAAG AACAAGCTGG ATTTTCTCCG CCCATACACA GTGCCCAACA AGAAGGGGAC      720

CAGGCTTKGC CGGTACAGGT GTGAGAAAGG GACTWCTGCA GTCCTNACTG NGAAATTACT     780

CCNCTTGNGA TTTNAGGTNC TTGAGNACAG TCAAACAATT GGCANTTCNT GAATTGGATT     840

AA                                                                   842

(2) INFORMATION FOR SEQ ID NO:3:

(i) SEQUENCE CHARACTERISTICS:
          (A) LENGTH: 248 amino acids
          (B) TYPE: amino acid
          (C) STRANDEDNESS: single
          (D) TOPOLOGY: linear (ii) MOLECULE TYPE: peptide (vii) IMMEDIATE SOURCE:
          (A) LIBRARY:
          (B) CLONE: Consensus (xi) SEQUENCE DESCRIPTION: SEQ ID NO:3:

Met Ser Tyr Asp Arg Ala Ile Thr Val Phe Ser Pro Asp Gly His Leu
 1               5                  10                  15

Phe Gln Val Glu Tyr Ala Gln Glu Ala Val Lys Lys Gly Ser Thr Ala
            20                  25                  30

Val Gly Val Arg Gly Arg Asp Ile Val Leu Gly Val Glu Lys Lys
        35                  40                  45

Ser Val Ala Lys Leu Gln Asp Glu Arg Thr Val Arg Lys Ile Cys Ala
    50                  55                  60

Leu Asp Asp Asn Val Cys Met Ala Phe Ala Gly Leu Thr Ala Asp Ala
65                  70                  75                  80

Arg Ile Val Ile Asn Arg Ala Arg Val Glu Cys Gln Ser His Arg Leu
                85                  90                  95
```

```
Thr Val Glu Asp Pro Val Thr Val Glu Tyr Ile Thr Arg Tyr Ile Ala
            100                 105                 110

Ser Leu Lys Gln Arg Tyr Thr Gln Ser Asn Gly Arg Arg Pro Phe Gly
            115                 120                 125

Ile Ser Ala Leu Ile Val Gly Phe Asp Phe Asp Gly Thr Pro Arg Leu
            130                 135                 140

Tyr Gln Thr Asp Pro Ser Gly Thr Tyr His Ala Trp Lys Ala Asn Ala
145                 150                 155                 160

Ile Gly Arg Gly Ala Lys Ser Val Arg Glu Phe Leu Glu Lys Asn Tyr
                165                 170                 175

Thr Asp Glu Ala Ile Glu Thr Asp Asp Leu Thr Ile Lys Leu Val Ile
            180                 185                 190

Lys Ala Leu Leu Glu Val Val Gln Ser Gly Gly Lys Asn Ile Glu Leu
            195                 200                 205

Ala Val Met Arg Arg Asp Gln Ser Leu Lys Ile Leu Asn Pro Glu Glu
            210                 215                 220

Ile Glu Lys Tyr Val Ala Glu Ile Glu Lys Glu Lys Glu Asn Glu
225                 230                 235                 240

Lys Lys Lys Gln Lys Lys Ala Ser
            245
```

(2) INFORMATION FOR SEQ ID NO:4:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:4:

```
GGCAGCGCAG GACACGGCGC CGAGGGTGGK GCGCGGGCGT AGTGGCGCCG GGAGTCGCGG      60

GTGCGCGCGG GCCGTGAGTG TGCGCTTTTG AGAGTCGCGG CGGAAGGAGC CCGGCCGCCG     120

CCCGCCGGCA TGAGCTACGA CCGCGCCATC ACCGTCTTCT CGCCCGACGG CCACCTCTTC     180

CAAGTGGAGT ACGCGCAGGA GGCCGTCAAG AAGGGCTCGA CCGCGGTTGG TGTTCGAGGA     240

AGAGACATTG TTGTTCTTGG TGTGGAGAAG AAGTCAGTGG CCAAACTGCA GGATGAAAGA     300

ACAGTGCGGA AGATCTGTGC TTTGGATGAC AACGTCTGCA TGGCCTTTGC AGGCTTAACC     360

GCCGATGCAA GGATAGTCAT CAACAGGGCC CGGGTGGAGT GCCAGAGCCA CCGGCTGACT     420

GTGGAGGACC CGGTCACTGT GGAGTACATC ACCCGCTACA TCGCCAGTCT GAAGCAGCGT     480

TATACGCAGA GCAATGGGCG CAGGCCGTTT GGCATCTCTG CCCTCATCGT GGGTTTCGAC     540

TTTGATGGCA CTCCTAGGCT CTATCAGACT GACCCCTCGG GCACATACCA TGCCTGGAAG     600

GCCAATGCCA TAGGCCGGGG TGCCAAGTCA GTGCGTGAGT TCCTGGAGAA GAACTATACT     660

GACGAAGCCA TTGAAACAGA TGATCTGACC ATTAAGCTGG TGATCAAGGC ACTCCTGGAA     720

GTGGTTCAGT CAGGTGGCAA AAACATTGAA CTTGCTGTCA TGAGGCGAGA TCAATCCCTC     780

AAGATTTTAA ATCCTGAAGA AATTGAGAAG TATGTTGCTG AAATTGAAAA AGAAAAAGAA     840

GAAAACGAAA AGAAGAAACA AAAGAAAGCA TCATGATGAA TAAAATGTCT TGCTTGTAA      900

TTTTTAAATT CATATCAATC ATGGATGAGT CTCGATGTGT AGGCCTTTCC ATTCCATTTA     960

TTCACACTGA GTGTCCTACA ATAAACTTCC GTATTTTTAA CCTGT                    1005
```

(2) INFORMATION FOR SEQ ID NO:5:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 307307

(xi) SEQUENCE DESCRIPTION: SEQ ID NO:5:

```
Met Leu Lys Pro Ala Leu Glu Pro Arg Gly Gly Phe Ser Phe Glu Asn
 1               5                  10                  15

Cys Gln Arg Asn Ala Ser Leu Glu Arg Val Leu Pro Gly Leu Lys Val
                20                  25                  30

Pro His Ala Arg Lys Thr Gly Thr Thr Ile Ala Gly Leu Val Phe Gln
             35                  40                  45

Asp Gly Val Ile Leu Gly Ala Asp Thr Arg Ala Thr Asn Asp Ser Val
         50                  55                  60

Val Ala Asp Lys Ser Cys Glu Lys Ile His Phe Ile Ala Pro Lys Ile
 65                  70                  75                  80

Tyr Cys Cys Gly Ala Gly Val Ala Ala Asp Ala Glu Met Thr Thr Arg
                 85                  90                  95

Met Val Ala Ser Lys Met Glu Leu His Ala Leu Ser Thr Gly Arg Glu
                100                 105                 110

Pro Arg Val Ala Thr Val Thr Arg Ile Leu Arg Gln Thr Leu Phe Arg
            115                 120                 125

Tyr Gln Gly His Val Gly Ala Ser Leu Ile Val Gly Gly Val Asp Leu
        130                 135                 140

Thr Gly Pro Gln Leu Tyr Gly Val His Pro His Gly Ser Tyr Ser Arg
145                 150                 155                 160

Leu Pro Phe Thr Ala Leu Gly Ser Gly Gln Asp Ala Ala Leu Ala Val
                165                 170                 175

Leu Glu Asp Arg Phe Gln Pro Asn Met Thr Leu Glu Ala Ala Gln Gly
                180                 185                 190

Leu Leu Val Glu Ala Val Thr Ala Gly Ile Leu Gly Asp Leu Gly Ser
            195                 200                 205

Gly Gly Asn Val Asp Ala Cys Val Ile Thr Lys Thr Gly Ala Lys Leu
        210                 215                 220

Leu Arg Thr Leu Ser Ser Pro Thr Glu Pro Val Lys Arg Ser Gly Arg
225                 230                 235                 240

Tyr His Phe Val Pro Gly Thr Thr Ala Val Leu Thr Gln Thr Val Lys
                245                 250                 255

Pro Leu Thr Leu Glu Leu Val Glu Glu Thr Val Gln Ala Met Glu Val
            260                 265                 270

Glu
```

(2) INFORMATION FOR SEQ ID NO:6:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (vii) IMMEDIATE SOURCE:
    (A) LIBRARY: GenBank
    (B) CLONE: 1089797

(xi) SEQUENCE DESCRIPTION: SEQ ID NO:6:

```
Met Ser Tyr Asp Arg Ala Ile Thr Val Phe Ser Pro Asp Gly His Leu
 1               5                  10                  15

Phe Gln Val Glu Tyr Ala Gln Glu Ala Val Lys Lys Gly Ser Thr Ala
                20                  25                  30

Val Gly Val Arg Gly Arg Asp Ile Val Val Leu Gly Val Glu Lys Lys
                35                  40                  45

Ser Val Ala Lys Leu Gln Asp Glu Arg Thr Val Arg Lys Ile Cys Ala
 50                  55                  60

Leu Asp Asp Asn Val Cys Met Ala Phe Ala Val Val Ala Ser Val Ser
65                   70                  75                  80

Gly Leu Thr Ala Asp Ala Arg Ile Val Ile Asn Arg Ala Arg Val Glu
                85                  90                  95

Cys Gln Ser His Arg Leu Thr Val Gly Asp Pro Val Thr Val Glu Tyr
                100                 105                 110

Ile Thr Arg Tyr Ile Ala Ser Leu Lys Gln Arg Tyr Thr Gln Ser Asn
                115                 120                 125

Gly Arg Arg Pro Phe Gly Ile Ser Ala Leu Ile Val Gly Phe Asp Phe
                130                 135                 140

Asp Gly Thr Pro Arg Leu Tyr Gln Thr Asp Pro Ser Gly Thr Tyr His
145                 150                 155                 160

Ala Trp Lys Ala Asn Ala Ile Gly Arg Gly Ala Lys Ser Val Arg Glu
                165                 170                 175

Phe Leu Glu Lys Asn Tyr Thr Asp Asp Ala Ile Glu Thr Asp Asp Leu
                180                 185                 190

Thr Ile Lys Leu Val Ile Lys Ala Leu Leu Glu Val Val Gln Ser Gly
                195                 200                 205

Gly Lys Asn Ile Glu Leu Ala Val Met Arg Arg Asp Gln Pro Leu Lys
                210                 215                 220

Ile Leu Ser Pro Glu Glu Ile Glu Lys Tyr Val Ala Glu Ile Glu Lys
225                 230                 235                 240

Glu Lys Glu Glu Asn Glu Lys Lys Lys Gln Lys Lys Ala Ser
                245                 250
```